Figure 1:
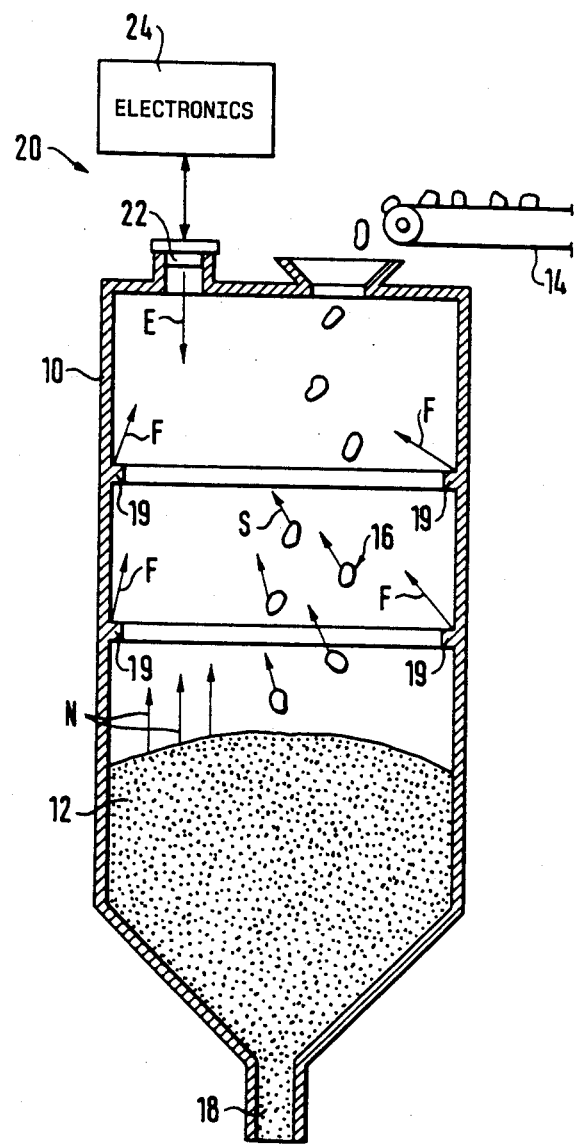

United States Patent [19]  [11] Patent Number: 4,972,386
Lau  [45] Date of Patent: Nov. 20, 1990

[54] FILLING LEVEL METER

[75] Inventor: Jürgen Lau, Weil am Rhein, Fed. Rep. of Germany

[73] Assignee: Endress u. Hauser GmbH u. Co., Fed. Rep. of Germany

[21] Appl. No.: 336,736

[22] Filed: Apr. 12, 1989

[30] Foreign Application Priority Data

Apr. 13, 1988 [DE] Fed. Rep. of Germany ....... 3812293

[51] Int. Cl.$^5$ .............................................. G01S 15/06
[52] U.S. Cl. .................................... 367/099; 367/908; 342/124; 73/290 V
[58] Field of Search .......................... 367/908, 901, 99; 181/123, 124; 340/621; 73/290 V, 490; 342/123, 124; 33/713, 719; 364/561, 562, 509

[56] References Cited

U.S. PATENT DOCUMENTS

| 3,939,465 | 2/1976 | Helton et al. ................. 367/901 X |
| 4,114,441 | 9/1978 | Magri . |
| 4,463,452 | 7/1984 | Chase, Jr. ..................... 367/901 X |
| 4,572,253 | 2/1986 | Farmer et al. ................ 367/908 X |
| 4,586,172 | 4/1986 | Vernet et al. . |
| 4,675,854 | 6/1987 | Lau ............................... 367/908 X |
| 4,700,569 | 10/1987 | Michalski et al. ........... 367/908 X |

FOREIGN PATENT DOCUMENTS

| 0093057 | 11/1983 | European Pat. Off. . |
| 1623971 | 9/1970 | Fed. Rep. of Germany . |
| 3337690 | 4/1985 | Fed. Rep. of Germany . |
| 3438045 | 5/1985 | Fed. Rep. of Germany . |
| 131671 | 7/1978 | German Democratic Rep. . |
| 613045 | 8/1979 | Switzerland . |
| 1550085 | 8/1979 | United Kingdom . |

Primary Examiner—Thomas H. Tarcza
Assistant Examiner—Tod R. Swann
Attorney, Agent, or Firm—Barnes & Thornburg

[57] ABSTRACT

The filling level meter for measuring the filling level in a container includes a transmitting and a receiving arrangement which directs sonic or ultrasonic pulses onto the filling material surface and receives the backscattered pulses reflected by the filling material surface and converts them to electrical reception signals. Connected to the transmitting and receiving arrangement is an evaluating circuit which in a signal processing path generates an envelope signal corresponding to the envelope of the reception signals, digitizes sampled values of the envelope signal, stores in a memory the digitized sampled values for creating a distance-dependent or travel-time-dependent amplitude profile of the measurement distance and evaluates the amplitude profile for determining the travel time of the most probable useful echo signal. Parallel to the signal processing path for generating the envelope signal, in the evaluating circuit a frequency detection of the echo signals is carried out by which echo signals having the transmission frequency of the sonic or ultrasonic pulses are determined. In dependence upon the result of the frequency detection the signal processing path is opened only for the echo signals having a frequency corresponding to the transmission frequency. As a result all the reception signals having a frequency not corresponding to the transmission frequency are excluded from the digitizing and further processing. Due to the Doppler frequency shift these include all the reception signals which are caused by reflections at moving obstacles. On the other hand, all reception signals having a frequency identical to the transmission frequency are passed on unchanged for the digitizing and further signal processing.

8 Claims, 3 Drawing Sheets

FILLING LEVEL METER

The invention relates to a filling level meter for measuring the filling level in a container comprising a transmitting and receiving arrangement which directs sonic or ultrasonic pulses onto the filling material surface and which receives backscattered pulses reflected from the filling material surface and converts said pulses to electrical reception signals and an evaluating circuit which is connected to the transmitting and receiving arrangement and which in a signal processing path generates an envelope signal corresponding to the envelope of the reception signals, digitizes sampled values of the envelope signal, stores the digitized sampled values in a memory for creating a distance-dependent or travel-time-dependent amplitude profile of the measurement distance and evaluates the amplitude profile for determining the travel time of the most probable useful echo signal.

In known filling level meters of this type by evaluating the digitized amplitude profile stored in the memory noise echo signals, in particular those which originate from fixed fittings in the container or are caused by multiple reflections at the filling material surface, can be distinguished from the useful echo signal so that erroneous measurements due to such noise echo signals are largely avoided. A substantial advantage of such filling level meters resides in that the amplitude profile of the measurement path is maintained. From the amplitude profile information on further parameters can be obtained which are decisive for the precise determination of the travel time of the sonic or ultrasonic waves in the container. It has however been found that the travel time measurement can still be impaired by noise echo signals originating from obstructions which move relatively to the filling level meter because such noise echo signals occur completely irregularly with continuously changing travel times. In the case of measurements in containers such noise or interference echo signals occur in particular by reflections at the filling stream or flow when filling material is introduced into the container from above simultaneously with the measurement.

In filling level meters of another type is it known to distinguish the echo signals originating from moving obstructions from the fixed target echo signals on the basis of the frequency shift caused by the Doppler effect in that the reception signals are sent through a frequency detecting stage. At the output of said frequency detecting stage however no amplitude information is available but only frequency information. This step thus cannot be applied when the amplitude profile of the measurement distance is to be stored and evaluated.

The problem underlying the invention is the provision of a filling level meter in which the travel time measurement is not impaired by noise echo signals originating from moving obstructions and the amplitude information of the echo signals originating from immovable obstructions is retained and the useful echo signals are distinguished from erroneous measurements.

According to the invention this problem is solved in that in the evaluating circuit parallel to the signal processing path for generating the envelope signal a frequency detection of the echo signals is effected by which echo signals with the transmitting frequency of the sonic or ultrasonic pulses are detected and that in dependence upon the result of the frequency detection the signal processing path is opened only for the echo signals having a frequency corresponding to the transmitting frequency.

In the filling level meter constructed according to the invention all the reception signals having a frequency which does not correspond to the transmitting frequency are excluded from the digitizing and further processing. Due to the Doppler frequency shift these include all the reception signals which are caused by reflections at moving obstacles. In contrast, all the reception signals having a frequency identical to the transmitting frequency are passed on unchanged for digitizing and further signal processing. Thus, the complete amplitude profile of said equifrequency reception signals is stored in the memory and is consequently available for the evaluation in the detection of the most probable useful echo signal and in the determination of the travel time.

Advantageous embodiments and further developments of the invention are characterized in the subsidiary claims.

Figure 2:
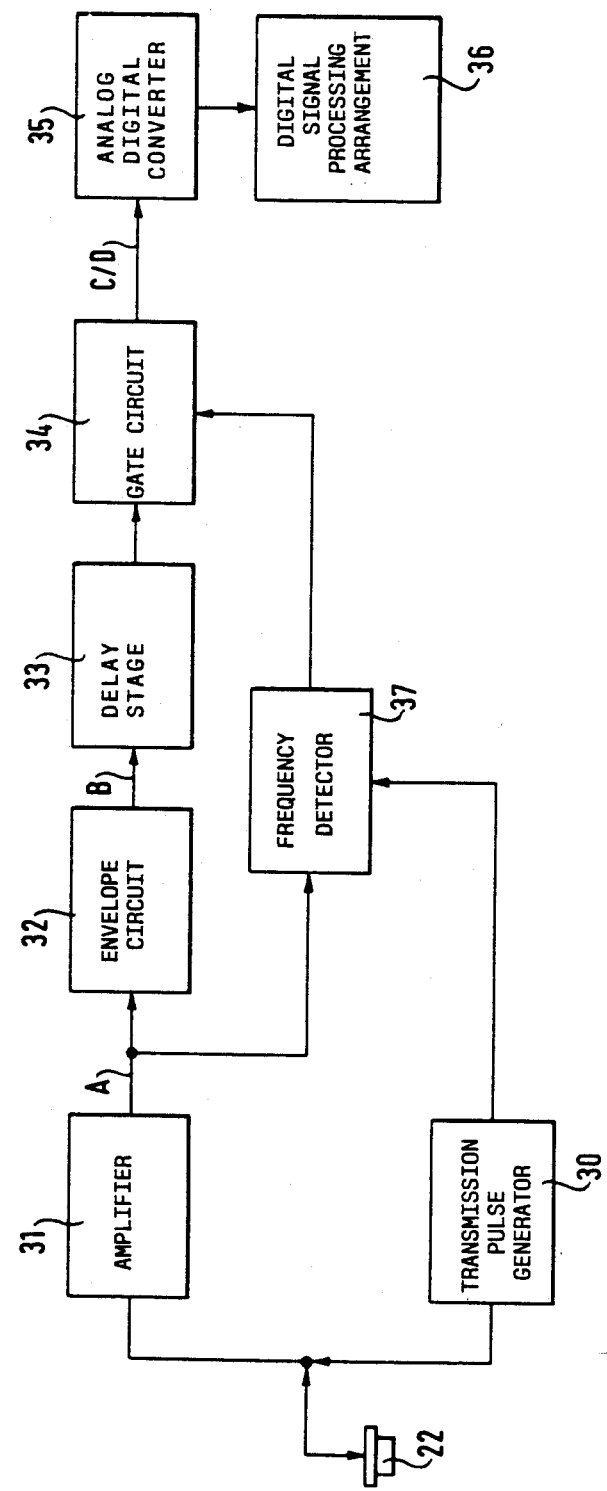
Figure 3:
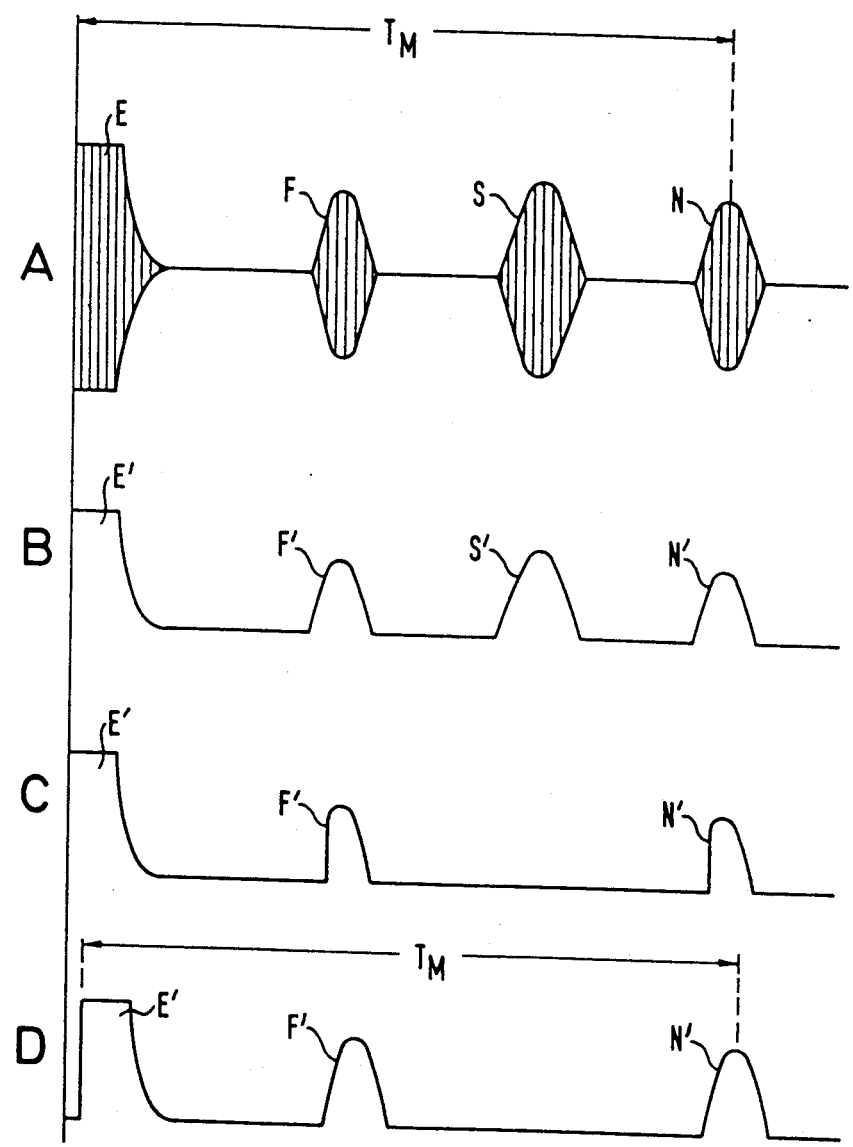

Further features and advantages of the invention will be apparent from the following description of an example of embodiment with the aid of the drawings, wherein:

FIG. 1 is a schematic illustration of the measurement in a container with the aid of a filling level meter, FIG. 2 is a block circuit diagram of the electronics of the filling level meter of FIG. 1 according to one embodiment of the invention and FIG. 3 shows time diagrams of signals which can occur in the electronics of FIG. 2.

FIG. 1 shows a container 10 which is partially filled with a bulk filling material 12. The filling material 12 may be pulverulent or granular or consist of even coarser pieces. It is introduced from above into the container 10, for example by means of a conveyor belt 14 from which it drops into the container as filling flow 16 and it can be withdrawn through a controllable removal opening 18 at the lowermost point of the container 10. Furthermore, a few fixed obstructions 19 are shown in the container 10.

For the continuous measurement, above the container 10 a filling level meter 20 is disposed which sends sonic or ultrasonic pulses downwardly into the container 10 and receives the echo pulses reflected at the surface of the filling material 12. The time interval between the transmission of a sonic or ultrasonic pulse and the reception of an echo pulse corresponds to the sound travel time from the filling level meter 20 to the filling material surface and back to the filling level meter. If the velocity of sound is known it is possible to calculate therefrom the distance of the filling material surface from the filling level meter and thus determine the filling level in the container 10.

The filling level meter 20 consists usually of an electroacoustic transducer 22 and the associated electronics 24.

The electroacoustic transducer 22 serves alternately as transmission transducer for sending sonic or ultrasonic transmission pulses and in each pause between two transmission pulses as reception transducer which converts the reflected echo pulses to electrical reception signals. The time interval between two consecutive transmission pulses is greater than the greatest travel time occurring of a sonic or ultrasonic pulse from the filling level meter up to the filling material surface and back. The electronics 24 contain circuits which at periodic intervals of time stimulate the electroacoustic transducer 22 to emit transmission pulses, circuits for amplifying and processing the electrical reception signals furnished by the electroacoustic transducer 22 and circuits for determining the desired filling level from the time interval between the transmission pulses and the received echo pulses. Generally, it is desired to determine not only the travel time of the sonic or ultrasonic pulses but also the form and amplitude of the reception signals furnished by the electroacoustic transducer 22 because it is possible to determine therefrom information on the conditions in the container 10 which can be used to detect the most probable useful echo signal and for the precise travel time measurement. This additional information is derived from the envelope curve or timeamplitude profile of the reception signals furnished by the electroacoustic transducer 22.

In a manner known per se the electroacoustic transducer 22, which operates alternately as transmission transducer and as reception transducer, can also be replaced by two separate transducers, one of which serves solely as transmission transducer and the other solely as reception transducer.

A significant problem in this filling level measurement based on the echo-sounding principle is that apart from the useful echo pulses which are reflected at the surface of the filling material as indicated in FIG. 1 by the arrows N interference or noise echo pulses can also occur which are reflected from other obstacles in the container and superimpose themselves on the useful echo pulses. Whereas noise echo pulses originating from the fixed obstructions 19 in the container, as indicated by the arrows F, always have the same travel time and thus by evaluating the amplitude profile of the reception signals can easily be detected and eliminated, the echo signals which are reflected at the particles of the filling material flow 16 dropping into the container, as indicated in FIG. 1 by the arrows S, greatly interfere with the filling level measurement. Said noise echo signals S occur with continuously changing travel times in the entire travel time range.

FIG. 2 shows the block circuit diagram of an embodiment of the electronics 24 which makes it possible to eliminate the detrimental effect of the noise echo pulses originating from the filling flow 16 without losing the information contained in the envelope or time-amplitude profile of the reception signals. Diagrams A to D of FIG. 3 show the time profile of various signals which can occur at the circuit points of the circuit of FIG. 2 denoted by the same letters.

FIG. 2 again shows the electroacoustic transducer 22 which is connected to the output of a transmission pulse generator 30. At periodic intervals of time the transmission pulse generator 30 sends a pulse-shaped electrical oscillation train with the frequency of the sonic or ultrasonic pulse to be transmitted as excitation pulse to the electroacoustic transducer 22 which is thereby stimulated to transmit a sonic or ultrasonic transmission pulse. The duration of the sonic or ultrasonic transmission pulse is small compared with the duration of the transmission periods determined by the periodic intervals of time between the consecutive transmission pulses.

The electroacoustic transducer 22 is further connected to the input of an amplifier 31 which amplifies the electrical signals coming from the transducer 22. These signals first include pulses corresponding to the sonic or ultrasonic transmission pulses. After the decay of each transmission pulse the electroacoustic transducer 22 acts as reception transducer which converts the incident sonic or ultrasonic echo pulses to electrical reception signals which are likewise supplied to the amplifier 31. Since the level of the reception signals is small compared with the level of the transmission pulses the electrical signals corresponding to the transmission pulses are limited by suitable measures known per se to avoid overdriving of the amplifier 31.

The amplifier 31 thus furnishes at its output in each transmission period a signal as shown for example in diagram A of FIG. 3. The start of the measuring period is defined by the transmission pulse E whose amplitude has been limited. Whereas the electrical excitation pulse coming from the transmission pulse generator 30 is a rectangular pulse, an exponentially decaying pulse appears at the input of the amplifier 31 because the electroacoustic transducer 22 continues to oscillate when the excitation pulse has ceased.

After a time interval $T_M$, defined by the distance of the filling material surface from the electroacoustic transducer 22, from the start of the transmission pulse E a useful echo pulse N appears which corresponds to the sonic or ultrasonic echo pulse reflected at the filling material surface. Said useful echo pulse N is an oscillation train having the transmission frequency of the sonic or ultrasonic wave and an envelope curve which is rounded and deformed to a greater or lesser extent compared with the original rectangular form.

Between the transmission pulse E and the useful echo pulse N in the diagram A of FIG. 3 a noise echo pulse S is shown which has been reflected by the filling flow 16 falling into the container as well as a noise echo pulse F which has been reflected at a fixed obstacle 19 in the container 10. Of course, in this section of the transmission period numerous other noise echo pulses S of this type may be present which with different travel times originate from different parts of the filling flow 16 as well as noise echo pulses F which have been reflected at fixed obstacles in the container. Due to multiple reflections noise or interference echo pulses can also appear after the useful echo pulse N.

The amplifier 31 is followed by an envelope circuit 32 which is constructed so that at its output it furnishes a signal corresponding to the envelope of its input signal. Envelope circuits which fulfil this function are generally known. In the simplest case the envelope circuit may be an amplitude demodulator which rectifies the amplitude-modulated carrier oscillation with the frequency of the sonic or ultrasonic wave and suppresses said oscillation by low-pass filtering. When the signal illustrated in diagram A is supplied to the input of the envelope circuit 32 at the output thereof the low-frequency signal of the diagram B then appears and contains the envelope E' of the transmission pulse E, the envelope N' of the useful echo pulse N and the envelopes F' and S' of the noise echo pulses F and S respectively. The envelope signal represents quite generally the time-amplitude profile of the output signal of the electroacoustic transducer 22 and also contains the entire amplitude information of the reception signal. Since the envelope signal is low-frequency it can be more easily processed and also transmitted with less expenditure over longer distances, for example to an evaluating apparatus which is arranged at a point remote from the container 10.

The envelope signal furnished by the output of the envelope circuit 32 is supplied in the circuit of FIG. 2 via a delay stage 33 and a gate circuit 34 to an analog-digital converter 35. In the analog-digital converter 35 the envelope signal is periodically sampled and each sampled value is converted to a digital signal in the form of a code group with a number of digits corresponding to the desired resolution.

The output of the analog-digital converter 35 is connected to a digital signal processing arrangement 36 which can be formed for example by a suitably programmed microcomputer. The digital signal processing arrangement 36 includes a memory in which are stored the code groups furnished by the analog-digital converter 35 and representing the digitized reception signal of at least one transmission period, preferably however of a plurality of consecutive transmission periods, so that in the memory a distance-dependent or travel-time-dependent amplitude profile of the measurement distance is disposed. This amplitude profile is then statistically smoothed and analyzed by empirical values. On the basis of this analysis the noise echoes F originating from fixed obstacles 19 are detected and the echo pulse determined which with the greatest probability represents the useful echo pulse reflected at the filling material surface and finally the travel time of said most probable useful echo pulse is determined for obtaining the filling level. This echo evaluation makes it possible to control the disadvantageous effects which occur with certain reception conditions, such as double or multiple reflections, noise echoes of fittings in the container or the like. However, the measurement can be made very difficult or even impossible in the presence of massive interferences by the irregular noise echo pulses S caused by the filling flow.

To avoid such interferences by the noise echo pulses originating from the filling flow the circuit of FIG. 2 contains a frequency detector 37 which is connected in parallel with the signal processing path containing the envelope circuit 32 to the output of the amplifier 31. A second input of the frequency detector 37 is connected to the transmission pulse generator 30 and the output of the frequency detector 37 is connected to the control input of the gate circuit 34. The frequency detector 37 receives from the transmission pulse generator a signal having the frequency of the transmission pulses and it continuously compares the frequency of the reception signal appearing at the output of the amplifier 31 with said transmission frequency. When the frequency detector 37 detects identity of the frequency of the reception signal and the transmission frequency it delivers to the control input of the gate circuit 34 a control signal which opens the gate circuit 34 so that the latter allows through to the analog-digital converter 35 the envelope signal transmitted via the delay stage 33. If however no identity exists between the frequency of the reception signal and the transmission frequency the gate circuit 34 is blocked by the output signal of the frequency detector 37.

The effect of the frequency detector 37 in conjunction with the gate circuit 34 is that the envelope signals S' of the noise echo pulses S originating from the filling flow 16 do not reach the analog-digital converter. The fact utilized here is that the filling current 16 is moving relatively to the echo-sounding device 20 so that the echo pulses reflected at the filling flow 16 undergo a frequency shift with respect to the transmission frequency due to the Doppler effect. The frequency detector 37 must of course be constructed so that it responds to this slight Doppler frequency shift and modifies the control signal furnished at the output in such a manner that the gate circuit 34 is blocked.

In contrast, the echo pulses F and N reflected at fixed obstacles and at the filling material surface have the transmission frequency because these reflection surfaces are at rest relatively to the filling level meter. The envelope signals F', N' corresponding to these echo pulses are therefore allowed to pass by the gate circuit 34 to the analog-digital converter 35.

The diagram C of FIG. 3 shows the output signal of the gate circuit 34, assuming that the delay stage 33 is not present. In this output signal the envelope S' of the interference echo pulse S is completely suppressed. However, the frequency detector 37 requires a certain time until it has detected the frequency identity of its two input signals with adequate accuracy because it must compare several oscillations. The opening of the gate circuit 34 is thus effected only a certain time after the start of the useful echo pulse so that the initial part of the envelope N' is clipped off. This can lead to falsification of the amplitude information.

This phenomenon is eliminated by the delay stage 33. It imparts to the envelope signal a delay which corresponds to the time required by the frequency detector 37 for the frequency detection. Thus it is achieved that the gate circuit 34 is already open when the start of the envelope curve N' of the useful echo pulse N arrives at the gate circuit. The output signal of the gate circuit 34 then corresponds to the diagram D of FIG. 3. It contains the complete envelope of the useful echo pulse N and also the envelopes of the noise or interference echo pulses F and other components of the reception signal which have the transmission frequency whilst the envelopes of all the signal components having a frequency deviating from the transmission frequency are suppressed.

It is then not the time-amplitude profile of the entire reception signal which is stored in the memory of the digital signal processing arrangement 36 but the time-amplitude profile of the echo signals which have the original transmission frequency.

The signal delay effected by the delay stage 33 has no effect on the travel time measurement because the envelope signal corresponding to the transmission pulse E and the envelope signal corresponding to the useful echo pulse N are delayed in the same manner so that the time interval $T_M$ decisive for the travel time measurement remains unchanged.

Various modifications of the circuit described will be obvious to the expert. For example, the delay stage 33 and the gate circuit 34 could be arranged in front of the envelope circuit 32 instead of behind it.

I claim:

1. Filling level meter for measuring the level of a material situated in a container comprising a transmitting and receiving arrangement which directs sonic or ultrasonic pulses onto the filling material surface and which receives backscattered pulses reflected from the filling material surface and converts said pulses to electrical reception signals and an evaluating circuit which is connected to the transmitting and receiving arrangement and which in a signal processing path generates an envelope signal corresponding to the envelope of the reception signals, digitizes sampled values of the envelope signal, stores the digitized sampled values in a memory for creating a distance-dependent or travel-time-dependent amplitude profile of the measurement distance and evaluates the amplitude profile for determining the travel time of the most probable useful echo signal, said evaluating circuit comprising means connected in parallel to said signal processing path for effecting a frequency detection of the echo signals whereby an identity of the frequency of the reception signals with the transmitting frequency is detected, said signal processing path being opened in dependence upon the result of the frequency detection only for the reception signals having a frequency corresponding to the transmitting frequency.

2. Filling level meter according to claim 1, wherein said evaluating circuit includes a frequency detector connected in parallel with the signal processing path and said signal processing path comprises a gate circuit controlled by the output signal of the frequency detector.

3. Filling level meter according to claim 2, wherein said signal processing path comprises a delay circuit which is inserted behind the connection point of the frequency detector and ahead of the gate circuit.

4. Filling level meter according to claim 2, wherein said gate circuit in the signal processing path lies behind the envelope circuit forming the envelope signal from the reception signals.

5. A system for measuring the level of a material situated inside a container, the system comprising transducer means for transmitting electrical pulses having a predetermined frequency onto the material inside the container, the transducer means receiving echo pulses reflected back to the transducer means from the material and converting the echo pulses received into an electrical reception signal, envelope generating means coupled to the transducer means for generating an envelope signal corresponding to the envelope of the reception signal, a frequency detector connected to the transducer means in parallel with the envelope generating means, the frequency detector comparing the frequency of the reception signal with the predetermined frequency of the electrical pulses transmitted by the transducer means, gate means coupled to the envelope generating means and the frequency detector for blocking the envelope signal upon detection of unequal frequencies by the frequency detector, the gate means permitting the envelope signal to pass through the gate mans upon detection of equal frequencies by the frequency detector, and means coupled to the gate means for processing the envelope signals passing through the gate means to determine the level of the material inside the container.

6. The system of claim 5, further comprising delay means situated between the envelope generating means and the gate means for delaying the envelope signal by a predetermined time to permit the frequency detector to compare the frequency of the reception signal and the frequency of the transmitted pulses and to generate a control signal for opening or closing the gate means before the envelope signal reaches the gate means.

7. The system of claim 5, wherein the processing means includes means for converting the envelope signal to a digital signal and means for storing the digital signal to create an amplitude profile of the digital signal.

8. The system of claim 7, wherein the processing means further comprises means for evaluating the amplitude profile to determine the level of material inside the container.

* * * * *